United States Patent
Xu et al.

(10) Patent No.: US 9,127,072 B2
(45) Date of Patent: Sep. 8, 2015

(54) METHODS OF TREATING HEMOPHILIA USING MONOCLONAL ANTIBODIES AGAINST ACTIVATED PROTEIN C

(75) Inventors: Jun Xu, Edmond, OK (US); Charles Esmon, Oklahoma City, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 816 days.

(21) Appl. No.: 13/306,301

(22) Filed: Nov. 29, 2011

(65) Prior Publication Data

US 2012/0164150 A1 Jun. 28, 2012

Related U.S. Application Data

(62) Division of application No. 12/257,706, filed on Oct. 24, 2008, now Pat. No. 8,153,766.

(60) Provisional application No. 60/983,092, filed on Oct. 26, 2007.

(51) Int. Cl.
*A61K 39/40* (2006.01)
*C07K 16/40* (2006.01)

(52) U.S. Cl.
CPC ............. *C07K 16/40* (2013.01); *C07K 2317/21* (2013.01); *C07K 2317/77* (2013.01)

(58) Field of Classification Search
None
See application file for complete search history.

(56) References Cited

U.S. PATENT DOCUMENTS

| 5,202,253 | A | * | 4/1993 | Esmon et al. | ................. | 435/331 |
| 5,279,956 | A | | 1/1994 | Griffin et al. | ................. | 435/183 |
| 6,953,568 | B1 | | 10/2005 | Esmon et al. | | |
| 6,989,241 | B2 | | 1/2006 | Esmon et al. | ................. | 435/7.4 |
| 7,247,453 | B1 | * | 7/2007 | Rezaie et al. | ................. | 435/69.6 |

FOREIGN PATENT DOCUMENTS

| WO | WO 93/00102 | 1/1993 |
| WO | WO 96/05303 | 2/1996 |
| WO | WO 02/29015 | 4/2002 |
| WO | WO 2006/052591 | 5/2006 |

OTHER PUBLICATIONS

The Merck Manuals Online Medical Library, [online]. Whitehouse Station, NJ: Merck Research Laboratories, 2006-2007. [retrieved on Nov. 19, 2007]. Retrieved from the Internet: < URL: http://www.merck.com/mmpe/print/sec06/ch068/ch068a.html>. Sepsis and Septic Shock. see pp. 1-5.*
Office Communication issued in Russian Patent Application No. 2010121148/10, dated Apr. 7, 2014. (English translation of Russian patent document).
Liaw et al., "A monoclonal antibody against activated protein C allows rapid detection of activated protein C in plasma and reveals a calcium ion dependent epitope involved in factor Va inactivation," *J Throbm. Haemost.*, 1(4):662-70, 2003.
Zhang and Castellino, "Generation of an antibody with a designed specificity difference for protein C and activated protein C," *J. Protein Chem.*, 8(4):471-480, 1989. (Abstract only).
Liaw et al., "Identification of the Protein C/Activated Protein C Binding Sites on the Endothelial Cell Protein C Receptor," *The Journal of Biological Chemistry*, vol. 276, No. 11, pp. 8364-8370, 2001.
Office Communication issued in Australian Patent Application No. 2013202464, dated Jul. 29, 2014.
Stearns-Kurosawa et al.,, "The endothelial cell protein C receptor augments protein C activation by the thrombin-thrombomodulin complex" *Proc. Natl. Acad. Sci. USA*, vol. 93, pp. 10212-10216, 1996.
Xu et al., "Reconstitution of the Human Endothelial Cell Protein C Receptor with Thrombomodulin in Phosphatidylcholine Vesicles Enhances Protein C Activation," *The Journal of Biological Chemistry*, vol. 274, No. 10, pp. 6704-6710, 1999.
Chognot et al., "Identification of protein C epitopes altered during its nanoencapsulation," *Journal of Protein Chemistry*, 18:779-784, 1999.
Green, "Antibody engineering via genetic engineering of the mouse: XenoMouse strains are a vehicle for facile generation of therapeutic human monoclonal antibodies," *J. Immunological Methods*, 231: 11-23, 1999.
Mosnier et al., "Activated protein C variants with normal cytoprotective but reduced anticoagulant activity," *Blood*, 104:1740-1744, 2004.
Office Communication issued in Israeli Patent Application No. 205284, dated Mar. 7, 2012.
Office Communication issued in Mexican Patent Application No. 83420, dated Oct. 11, 2011.
Office Communication issued in U.S. Appl. No. 12/257,706, dated Jun. 24, 2010.
Office Communication issued in U.S. Appl. No. 12/257,706, dated Nov. 15, 2010.
Office Communication issued in U.S. Appl. No. 12/257,706, dated Oct. 18, 2011.
Office Communication issued in U.S. Appl. No. 12/257,706, dated Mar. 15, 2011.
Owens and Young, "The genetic engineering of monoclonal antibodies," *J. Immunological Methods*, 168: 149-165, 1994.
PCT International Search Report and Written Opinion issued in Application No. PCT/US2008/081110, dated Jul. 8, 2009.
PCT International Partial Search Report issued in Application No. PCT/US2008/081110, dated Feb. 16, 2009.
Rezaie and Esmon, "The function of calcium in protein C activation by thrombin and the thrombin-thrombomodulin complex can be distinguished by mutational analysis of protein C derivatives," *J. Biol. Chem.*, 267:26104-26109, 1992.
Office Communication issued in Japanese Patent Application No. 2012-263561, dated Mar. 5, 2014. (English translation of Japanese text).
Preston et al., "Multifunctional specificity of the protein C/activated protein C Gla domain," *J. Biol. Chem.*, 281(39):28850-7, 2006.

* cited by examiner

*Primary Examiner* — Sharon Wen
(74) *Attorney, Agent, or Firm* — Parker Highlander PLLC

(57) ABSTRACT

The present invention provides monoclonal antibodies that selectively bind to and inhibit activated protein C without binding to or inhibiting unactivated protein C. Other antibodies inhibit both activated protein C and activation of unactivated protein C. Methods of treatment employing these antibodies are described herein as are methods of screening for and detecting these antibodies.

1 Claim, 15 Drawing Sheets

A
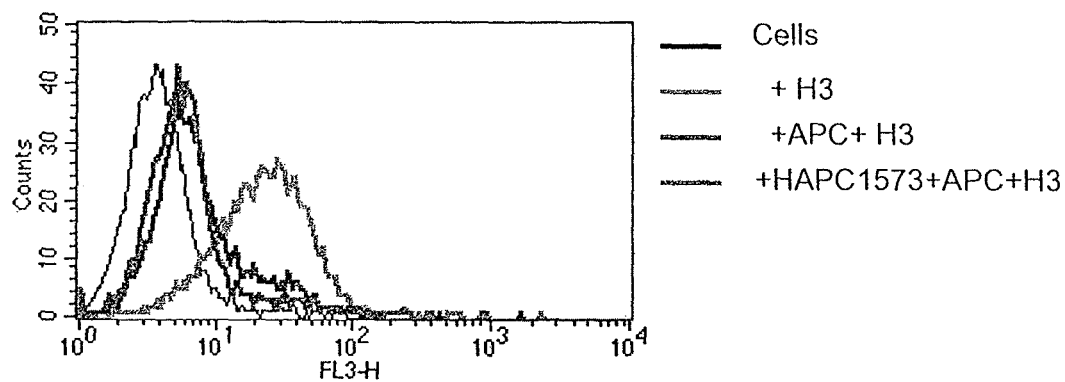
B
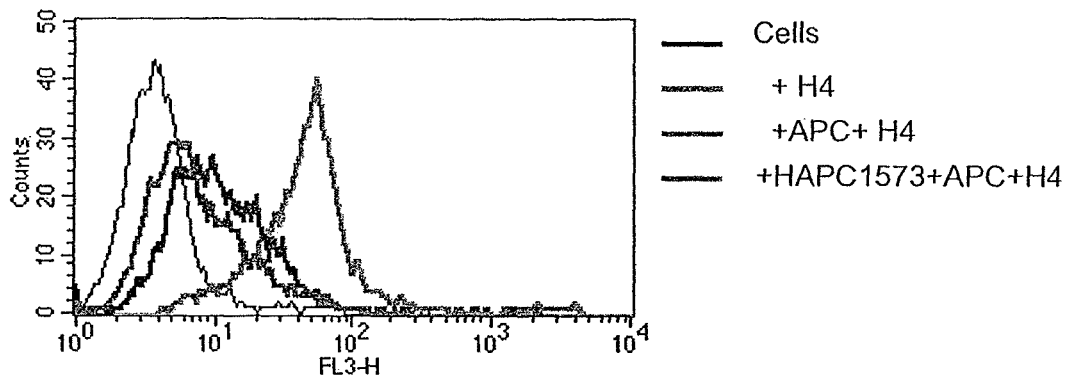
FIG. 7A-B

A
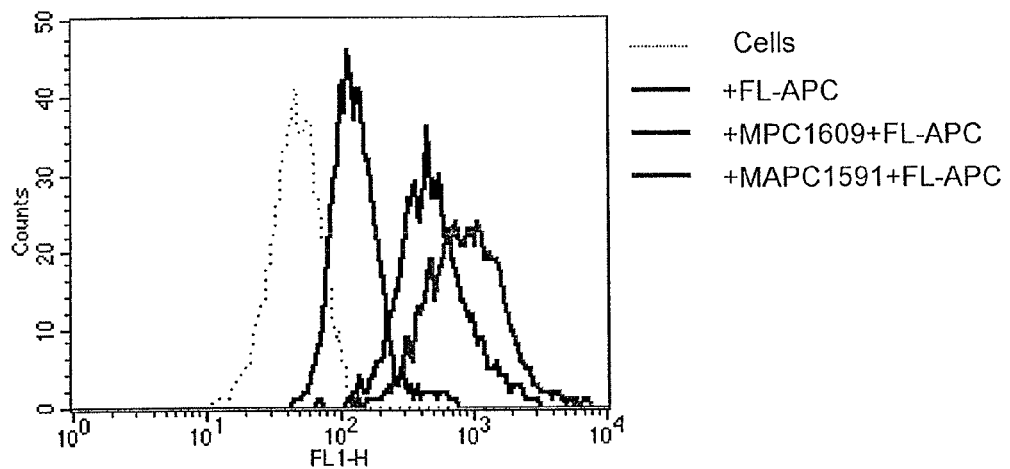
B
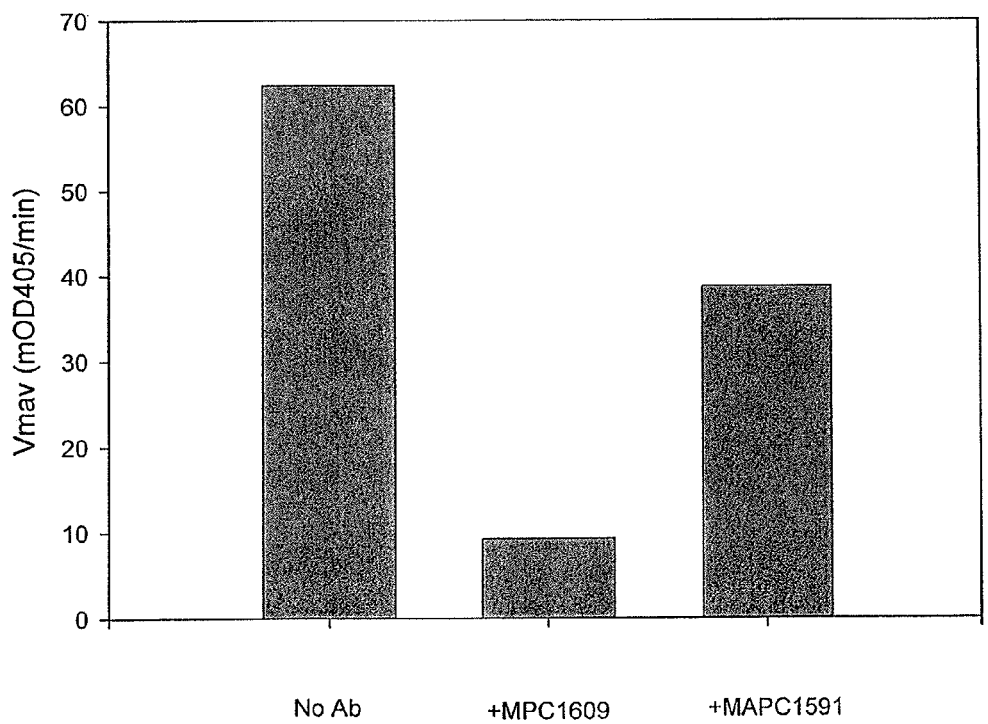
FIG. 8A-B

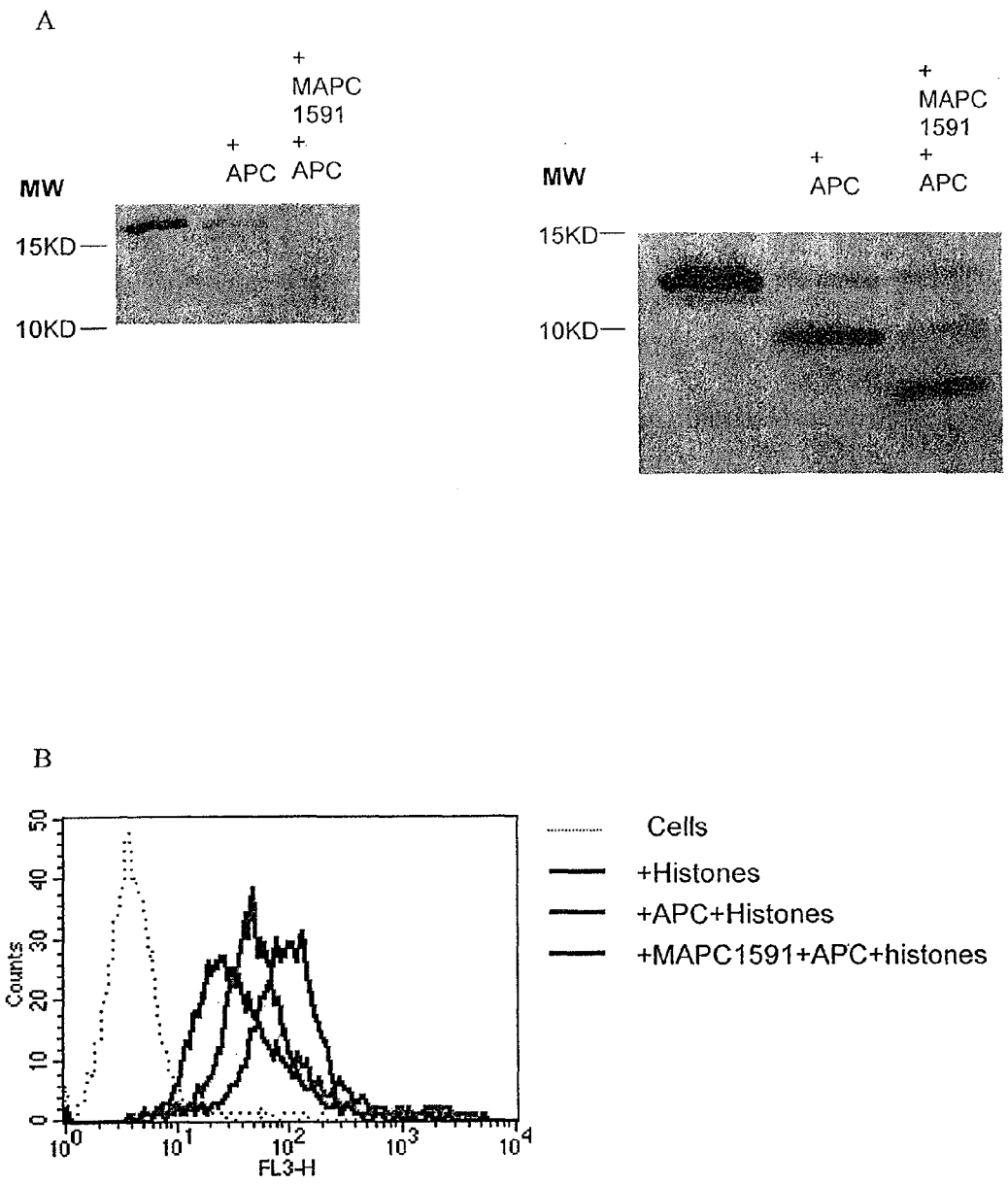
FIG. 11A-B

METHODS OF TREATING HEMOPHILIA USING MONOCLONAL ANTIBODIES AGAINST ACTIVATED PROTEIN C

The present invention is a divisional of co-pending application Ser. No. 12/257,706, filed Oct. 24, 2008, which claims benefit of priority to U.S. Provisional Application Ser. No. 60/983,092, filed Oct. 26, 2007, each of which is hereby incorporated by reference in their entirety.

BACKGROUND OF THE INVENTION

1. Field of the Invention

The present invention relates generally to the field of antibodies. More particularly, the present invention describes identification and use of monoclonal antibodies and antibody fragments selectively directed to activated protein C (APC).

2. Description of Related Art

Blood coagulation is a process consisting of a complex interaction of various blood components, or factors, which eventually give rise to a fibrin clot. Generally, blood components participating in the coagulation "cascade" are proenzymes or zymogens—enzymatically inactive proteins that are converted into an active form by action of an activator. Regulation of blood coagulation is largely accomplished enzymatically by proteolytic inactivation of the pro-coagulation factors Va and VIIIa achieved by activated protein C (APC) (Esmon, 1989).

Protein C is the precursor to APC, a potent natural anticoagulant. Protein C is activated by thrombin in complex with thrombomodulin (TM). The activation is augmented by endothelial cell protein C receptor (EPCR). TM and EPCR can be down-regulated due to inflammatory mediators, such as tumor necrosis factor, reviewed by Esmon (1999). TM and EPCR have also been found to be reduced in some forms of septic shock, meningococcemia in particular. Since EPCR and TM are expressed on endothelium, it is not possible to directly determine how well they are functioning without removal of blood vessels.

APC functions as an anticoagulant by proteolytically cleaving and downregulating pro-coagulant factors. APC also serves important functions as an anti-apoptosis agent, an anti-inflammatory molecule and a cytoprotectant. Bleeding disorders where homeostatis is dysregulated through a loss of a key factor, such as the absence of Factor VIII in heomphilia, or in trauma patients where the wound process results in a temporary loss of hemostasis, may be treated by the removal of APC. Such treatment, however, could result in unwanted detrimental consequences of removing the beneficial functions of APC in addition to the removal of the anti-coagulant activity. Therefore it is desirable to have a therapeutic that selectively targets the anti-coagulant activity of APC while leaving other functions of the molecule intact.

SUMMARY OF THE INVENTION

A method for treating bleeding disorders has been developed and described herein involving the use of a monoclonal antibody which recognizes activated protein C, but does not recognized unactivated protein C. In this regard, the present invention also provides monoclonal antibodies that selectively bind to and/or block the proteolytic active site of activated protein C. Such antibodies may inhibit the anticoagulant activity of activated protein C, but may not affect any activity of unactivated protein C, in certain embodiments. Such antibodies may also retain the cytoprotective effects of activated protein C, in certain embodiments. Thus, methods of the present invention also include treatments employing such monoclonal antibodies where it is desirable to selectively inhibit the anticoagulant activity of activated protein C.

Accordingly, certain general aspects of the present invention contemplate a monoclonal antibody, wherein said antibody binds to and inhibits activated protein C, but does not bind to or inhibit unactivated protein C. For example, certain embodiments of the present invention contemplate a monoclonal antibody, wherein said antibody binds to and inhibits activated protein C anticoagulant activity, but does not bind to or inhibit activation of unactivated protein C. In particular embodiments, a monoclonal antibody of the present invention is HAPC 1573. Antibodies of the present invention that bind to and inhibit activated protein C and its anti-coagulant activities may do so in vivo and/or in vitro.

Other monoclonal antibodies of the present invention are contemplated, such as an antibody that inhibits activated or unactivated protein C binding of endothelial cell protein C receptor (EPCR) or phospholipids and inhibits unactivated protein C activation. In certain aspects, such an antibody binds to the mouse unactivated protein C Gla-domain. Such antibodies may be employed in in vitro or in vivo contexts.

An antibody of the present invention may, for example, be a murine antibody, An antibody of the present invention may, for example, be a humanized antibody. An antibody of the present invention may be comprised in a pharmaceutical composition, wherein the pharmaceutical composition also comprises pharmaceutically acceptable carrier. An antibody of the present invention may also be used in methods wherein the antibody is contacted with a cell in vitro or in vivo.

Also contemplated by the present invention is a method of inhibiting activated protein C anticoagulant activity in a subject, comprising administering an effective amount of an antibody of the present invention to said subject (e.g., a mammal, such as a human). In this or any other method of the present invention involving the administration of an antibody of the present invention, the cytoprotective effects of activated protein C may, in certain embodiments, not be decreased, or may stay within normal levels.

Methods of inhibiting activated protein C amidolytic activity in a subject, comprising administering an effective amount of an antibody of the present invention to said subject, are also contemplated.

Also contemplated by the present invention is a method of treating a subject in need of blood coagulation comprising administering an effective amount of an antibody of the present invention to said subject. Such a subject could be suffering from, for example, hemophilia or hemorrhage.

A method of treating a subject suffering from sepsis comprising administrating an effective amount of an antibody of the present invention is also contemplated herein. Such methods may also employ administration of activated protein C.

Also contemplated are methods of treating a subject suffering from hemophilia comprising administrating an effective amount of an antibody of the present invention.

Antibodies of the present invention may also be employed, for example, in methods of modulating hemostasis in a subject or modulating thrombosis in a subject, comprising administrating an effective amount of an antibody of the present invention. Such methods may also employ administration of activated protein C.

Certain methods of the present invention contemplate a method of inhibiting activation of unactivated protein C activation comprising administering to a subject an effective amount of the monoclonal antibody of the present invention. Antibodies employed in such methods may also inhibit activated or unactivated protein C binding of endothelial cell protein C receptor (EPCR) or phospholipids.

A subject in accordance with present invention may, for example, be a mammal, such as a mouse, rat, rabbit, dog, horse, or human.

Unless otherwise noted, any antibody described herein may be an antibody fragment. For example, the antibody may be further defined as Fab', Fab, F(ab')$_2$, a single domain antibody, Fv, or scFv, which are all well-known types of antibody fragments. Unless otherwise noted, an antibody of the present invention also contemplates such fragments.

The term "antibody" is used to refer to any antibody like molecule that has an antigen binding region, and includes antibody fragments such as Fab', Fab, F(ab')2, single domain antibodies (DABs), Fv, scFv (single chain Fv), and the like, described below. The techniques for preparing and using various antibody based constructs and fragments are well known in the art. Means for preparing and characterizing antibodies are also well known in the art (see, e.g., Antibodies: A Laboratory Manual, Cold Spring Harbor Laboratory, 1988; incorporated herein by reference).

Another aspect of the invention contemplates the variable region that comprises alternating complementarity determining regions, or CDRs, and framework regions, or FRs. The CDRs are the sequences within the variable region that generally confer antigen specificity.

The invention also encompasses portions of antibodies that comprise sufficient variable region sequence to confer antigen binding. Portions of antibodies include, but are not limited to Fab, Fab', F(ab')$_2$, Fv, SFv, scFv (single-chain Fv), whether produced by proteolytic cleavage of intact antibodies, such as papain or pepsin cleavage, or by recombinant methods, in which the cDNAs for the intact heavy and light chains are manipulated to produce fragments of the heavy and light chains, either separately, or as part of the same polypeptide.

mAbs within the scope of the invention also include sequences corresponding to human antibodies, animal antibodies, and combinations thereof. The term "chimeric antibody," as used herein, includes antibodies that have variable regions derived from an animal antibody, such as a rat or mouse antibody, fused to another molecule, for example, the constant domains derived from a human antibody. One type of chimeric antibodies, "humanized antibodies," have had the variable regions altered (through mutagenesis or CDR grafting) to match (as much as possible) the known sequence of human variable regions. CDR grafting involves grafting the CDRs from an antibody with desired specificity onto the FRs of a human antibody, thereby replacing much of the non-human sequence with human sequence. Humanized antibodies, therefore, more closely match (in amino acid sequence) the sequence of known human antibodies. By humanizing mouse monoclonal antibodies, the severity of the human anti-mouse antibody, or HAMA, response is diminished. The invention further includes fully human antibodies which would avoid, as much a possible, the HAMA response. Production of humanized antibodies is described in more detail below.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "contact," when applied to a cell, is used herein to describe the process by which a compound of the invention is delivered to a target cell or is placed in direct juxtaposition with the target cell.

The term "effective," as that term is used in the specification and/or claims (e.g., "an effective amount," means adequate to accomplish a desired, expected, or intended result.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting," "reducing," or "prevention," or any variation of these terms, when used in the claims and/or the specification includes any measurable decrease or complete inhibition to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal.

Throughout this application, the term "about" is used to indicate that a value includes the inherent variation of error for the device or the method being employed to determine the value, or the variation that exists among the study subjects. For example, "about" can be within 10%, preferably within 5%, more preferably within 1%, and most preferably within 0.5%.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

It is contemplated that any embodiment discussed in this specification can be implemented with respect to any compound, method, or composition of the invention, and vice versa.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7. Effect of HAPC1573 on APC cytoprotection against histones.

FIGS. 8A-C. MPC1609 and MAPC1591 inhibit APC anticoagulant activity. (FIG. 8A) bEnd3 cells were incubated with 100 nM FL-APC in the absence or presence of 125 nM MPC1609 or MAPC1591 for 15 min on ice and subjected to flow cytometry. (FIG. 8B) bEnd3 cells were incubated with 100 nM protein C and 5 nM thrombin in the absence or presence of 100 nM MPC 1609 or MAPC1591 for 15 min at 37° C. and APC activity was measured by PCa chromogenic substrate. (FIG. 8C) One stage plasma clotting time was measured with 200 ng/ml in the absence or presence of 5 μg/ml MPC1609 or MAPC1591. Protein C activation and clotting assays were performed in duplicate and all errors were within 5%.

(FIG. 10A) Mouse body temperature, (FIG. 10B) serum IL-6, (FIG. 10C) serum BUN (FIG. 10D) and creatinine levels were measured 3 or 18 hrs after mice were challenged.

FIGS. 11A-C. MAPC1591 enhances APC cleaving histones. (FIG. 11A) 100 ug/ml calf thymus histone H3(left panel) or H4 (right panel) in Opti-MEM was incubated with or without 100 nM APC in the absence or presence of 200 nM MAPC1591 for 1 hr at 37° C. Samples were then subjected to SDS-PAGE and Commassie blue staining. (FIG. 11B) EA.hy926 cells were cultured with calf thymus histones (50 μg/ml) in the absence or presence of APC (100 nM) and MAPC1591 (200 nM) for 1 hr at 37° C. Cell death was measured by flow cytometry for PI (FL3) positive staining. (FIG. 11C) BL6 mice were injected intravenously with saline, 10 mg/kg LPS, or 10 mg/kg LPS with 10 mg/kg MAPC1591 or MPC1609. Plasma samples were taken 18 hrs post challenge and subjected to SDS-PAGE and Western blotting using goat anti-histone H3 antibody.

DESCRIPTION OF ILLUSTRATIVE EMBODIMENTS

Figure 1:
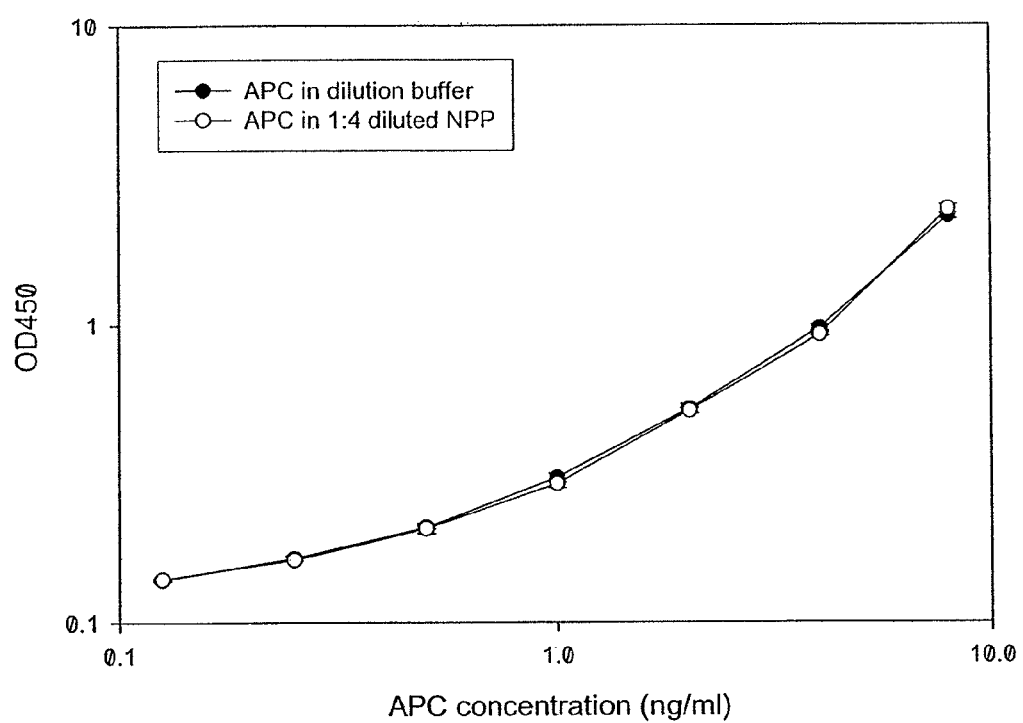
FIG. 1. APC ELISA standard curve.

The present invention relates to the discovery of monoclonal antibodies that selectively bind to activated protein C, but not unactivated protein C, and specifically inhibit the anti-coagulation activity of activated protein C. These and other aspects of the invention are described in greater detail below.

A. Antibody Structure

Antibodies comprise a large family of glycoproteins with common structural features. An antibody is comprised of four polypeptides that form a three dimensional structure which resembles the letter Y. Typically, an antibody is comprised of two different polypeptides, the heavy chain and the light chain. An antibody molecule is comprised of one or more Y-units, each Y comprising two heavy chains and two light chains.

An antibody molecule typically consists of three functional domains: the Fc, Fab, and antigen-binding site. The Fc domain is located at the base of the Y. The arms of the Y comprise the Fab domains. The antigen-binding site is located at the end of each arm of the Y. The area at the fulcrum of the arms of the Y is the hinge region.

There are five different types of heavy chain polypeptides designated as $\alpha$, $\delta$, $\epsilon$, $\gamma$, and $\mu$. There are two different types of light chain polypeptides designated $\kappa$ and $\lambda$. An antibody typically contains only one type of heavy chain and only one type of light chain, although any light chain can associate with any heavy chain.

The carboxyl terminal of each heavy chain polypeptide is known as the constant (Fc) region. The amino terminal of each heavy and light chain polypeptide is known as the variable (V) region. Within the variable regions of the chains are hypervariable regions known as complementarity determining regions (CDRs). The variable regions of one heavy chain and one light chain associate to form an antigen-binding site. Each heavy chain and each light chain includes three CDRs. The six CDRs of an antigen-binding site define the amino acid residues that form the actual binding site for the antigen. CDR variability accounts for the diversity of antigen recognition.

B. Preparation of Monoclonal Antibodies of the Present Invention

The present invention concerns the production and use of molecules that are capable of "specific binding" to one another. As used herein, a molecule is said to be capable of "specific binding" to another molecule, if such binding is dependent upon the respective structures of the molecules. The known capacity of an antibody to bind to an immunogen is an example of "specific binding." Such interactions are in contrast to non-specific binding that involve classes of compounds, irrespective of their chemical structure (such as the binding of proteins to nitrocellulose, etc.) Most preferably, an antibody of the present invention will exhibit "highly specific binding," such that they will be incapable or substantially incapable of binding to closely related heterologous molecules. Indeed, the preferred monoclonal antibodies of the present invention exhibit the capacity to bind to activated protein C, but are substantially incapable of binding unactivated protein C. In further embodiments, the monoclonal antibodies specifically inhibit only the anticoagulant activities of APC by binding to and blocking the proteolytic active site of APC.

Thus, in one embodiment, such molecules will comprise fragments (such as (F(ab'), F(ab')2) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule, or they may be capable of binding to an activated protein C epitope and a "non-activated protein C" epitope.

A monoclonal antibody can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides. Where azaserine is used, the medium is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with antigen-polypeptides. The selected clones can then be propagated indefinitely to provide the monoclonal antibody.

By way of specific example, to produce a monoclonal antibody, mice are injected intraperitoneally with between about 1-200 µg of an antigen comprising a polypeptide. B lymphocytes are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT medium (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection medium.

Each of the surviving hybridoma cells produces a single antibody. These cells are then screened for the production of the specific antibody immunoreactive with an antigen/polypeptide. Limiting dilution of the hybridomas isolates single cell hybridomas. The hybridomas are serially diluted many times and, after the dilutions are allowed to grow, the supernatant is tested for the presence of the monoclonal antibody. The clones producing that antibody are then cultured in large amounts to produce an antibody in convenient quantity.

Liaw et al. (2003), incorporated herein by reference in its entirety, described preparations of certain mouse monoclonal antibodies against human activated and human unactivated protein C.

Where the antibodies or their fragments are intended for therapeutic purposes, it may desirable to "humanize" them in order to attenuate any immune reaction. Such humanized antibodies may be studied in an in vitro or an in vivo context. Humanized antibodies may be produced, for example by replacing an immunogenic portion of an antibody with a corresponding, but non-immunogenic portion (i.e., chimeric antibodies). Robinson et al., PCT Application PCT/U.S.86/02269; Akira et al., EP Application 184,187; Taniguchi, EP Application 171,496; Morrison et al., EP Application 173, 494; Neuberger et al., PCT Application WO 86/01533; Cabilly et al., EP Application 125,023; Better et al. (1988); Liu et al. (1987); Liu et al. (1987); Sun et al. (1987); Nishimura et al. (1987); Wood et al. (1985); Shaw et al. (1988); all of which references are incorporated herein by reference. General reviews of "humanized" chimeric antibodies are provided by Morrison (1985) and by Oi et al. (1986); which references are incorporated herein by reference).

Suitable "humanized" antibodies can alternatively be produced by CDR or CEA substitution. Jones et al. (1986); Verhoeyan et al. (1988); Beidler et al. (1988); all of which references are incorporated herein by reference.

D. Pharmaceutical Compositions

Pharmaceutical compositions of the present invention comprise an effective amount of one or more antibodies, therapeutic agents or additional agent dissolved or dispersed in a pharmaceutically acceptable carrier. Aqueous compositions of the present invention comprise an effective amount of the antibody, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. For human administration, preparations should meet sterility, pyrogenicity, general safety and purity standards as required by FDA Office of Biologic Standards.

The biological material should be extensively dialyzed to remove undesired small molecular weight molecules and/or lyophilized for more ready formulation into a desired vehicle, where appropriate. The active compounds will then generally be formulated for parenteral administration, e.g., formulated for injection via the intravenous, intramuscular, sub-cutaneous, intranasal, intralesional, or even intraperitoneal routes. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The antibodies of the present invention can be formulated into a composition in a free base, in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly, concentrated solutions for direct injection is also contemplated, where the use of DMSO as solvent is envisioned to result in extremely rapid penetration, delivering high concentrations of the active agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intranasal, and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; liposomal formulations; time release capsules; and any other form currently used, including cremes.

In certain embodiments, the use of liposomes and/or nanoparticles is contemplated for the formulation and administration of the antibodies and/or analogs thereof. The formation and use of liposomes is generally known to those of skill in the art, and is also described below.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles are easily made.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200-500 Å, containing an aqueous solution in the core.

The following information may also be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

The therapeutic agent may comprise different types of carriers depending on whether it is to be administered in solid, liquid or aerosol form, and whether it needs to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, by inhalation (e.g., aerosol inhalation), by injection, by infusion, by continuous infusion, localized perfusion bathing target cells directly, via a catheter, via a lavage, in cremes, in lipid compositions (e.g., liposomes), or by other methods or any combination of the foregoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the antibodies are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations of the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

E. Kits

Any of the compositions described herein may be comprised in a kit. The kits will thus comprise, in suitable container means, an antibody and/or an additional agent of the present invention. The inventors envisage other components that may be included in a kit. Therapeutic kits of the present invention comprise in suitable container means, a pharmaceutically acceptable formulation of an antibody in a pharmaceutically acceptable formulation. The kit may have a single container means, and/or it may have distinct container means for each compound.

When the components of the kit are provided in one and/or more liquid solutions, the liquid solution is an aqueous solution, with a sterile aqueous solution being particularly preferred. The antibody may also be formulated into a syringeable composition, in which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the antibody/antibody formulation is placed, preferably, suitably allocated. The kits may also comprise a second container means for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate antibody within the body of an animal. Such an instrument may be a syringe, pipette, forceps, and/or any such medically approved delivery vehicle.

F. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Methods for Screening, Identification and Use of a Human MAb of the Present Invention Materials. Human protein C, bovine thrombin were prepared as described previously (Esmon et al., 1993; incorporated herein by reference in its entirety). Recombinant APC (Xigris) was from Eli Lilly. Spectroxyme PCa was from American Diagnostica. 1-Palmitoyl-2-oleoyl-phosphatidylcholine (PC), 1-palmitoyl-2-oleolylphosphatidylserine (PS), and 1-palmitoyl-2-oleolyl-phosphatidylethanolamine (PE) were from Avanti Polar Lipids, Inc. Human endothelial derived EA.hy926 cells were maintained in DMEM (Dulbecco's modified Eagle's medium) supplemented with 10% fetal bovine serum, L-glutamine and HAT (hypoxanthine, aminopterin, thymidine). Fluorescein labeled APC (FL-APC) was prepared with the Fluorescein-EX Protein Labeling Kit from Molecular Probes according to the manufacturer's instructions. In these examples, "protein C," without the "activated" modifier, refers to unactivated protiein C.

Generation of mouse anti-human protein C and APC monoclonal antibodies. Mouse monoclonal antibody (mAb) against human protein C or APC was developed by standard techniques (Rezaie and Esmon, 1992).

Screening for specific mAb for protein C or APC. Human protein C mAb 1575 and 1580 (HPC1575 and HPC1580) were obtained by screening the blocking ability of mAb for the binding of FL-APC to EA.hy926 cells by FACS. Briefly, EA.hy926 cells were incubated with 50 nM FL-protein C and 100 nM various monoclonal antibodies against protein C in HBSS (Hanks' Balanced Salt Solution) buffer containing 0.5% BSA, 3 mM $CaCl_2$ and 0.6 mM $MgCl_2$ for 30 min on ice, and subjected to FACS analysis. Human APC mAb 1573 (HAPC1573) was obtained by screening the binding ability of mAb to APC but not protein C with an ELISA assay. Briefly, a 96-well MaxiSorp plate (NUNC) was coated with 5 µg/ml different mAbs in 15 mM $Na_2CO_3$, 35 mM $NaHCO_3$, pH 9.6 buffer overnight at 4° C. The plate was washed with TTBS (TBS containing 0.05% Tween-20) containing 1 mM CaCl2 (TTBS calcium buffer), blocked with 0.1% gelatin in TBS (20 mM Tris-HCl, 150 mM NaCl, pH 7.5) for 1 hr, washed with TTBS calcium buffer again, incubated with 100 ng/ml protein C or APC in TTBS calcium buffer for 1 hr. After washing with TTBS calcium buffer, the plate was incubated with 2 μg/ml biotinylated HPC1580 for 1 hr, washed again with TTBS calcium buffer, incubated with 1 μg/ml streptavidin-alkaline phosphatase conjugate in TTBS calcium buffer for another hour. The endpoint absorbance at 405 nm was read on a Vmax microplate reader after final washing with TTBS calcium buffer and adding p-nitrophenyl phosphate liquid substrate (Sigma).

ELISA assay for APC in plasma. The assay was modified from the previously described ELISA assay for screening mAb against APC. Briefly, the plate was coated with 5 μg/ml HAPC1573, blocked with TBS containing 1× casein (Vector Lab) and washed again with TTBS calcium buffer. Spike recombinant APC from 0-8 ng/ml in TTBS containing 10 mM benzamidine, 1 mM EDAT and 0.25× casein buffer (Dilution buffer) or 1:4 diluted human plasma and incubate the samples in the plate for one hour. After washing with TTBS calcium buffer, the plate was incubated with 1 ug/ml biotinylated HPC1575 in TTBS containing 10 mM benzamidine, 5 mM CaCl2 and 0.25× casein buffer for one hr. After washing with TTBS calcium buffer, the plate was incubated with 0.5 μg/ml streptavidin-HRP in TTBS containing 10 mM benzamidine, 5 mM $CaCl_2$ and 0.25× casein buffer for another hour, washed again with TTBS calcium buffer, and color developed with Ultra-TMB substrate (Pierce). OD450 was read after adding 0.5 M H2SO4 to stop the HRP enzymatic reaction.

Influence of mAb on FL-APC binding on endothelium. EA.hy926 cells were incubated with 50 nM FL-APC in HBSS buffer containing 0.5% BSA, 3 mM CaCl2 and 0.6 mM MgCl2 in the absence or presence of HAPC1573 or HPC1575 in various concentrations for 30 min on ice, and subjected to FACS analysis.

Influence of mAb on APC anticoagulant activity in plasma clotting assay. The influence of mAb on APC anticoagulant activity in plasma was determined in a modified factor Xa one-stage clotting assay using ST4 coagulation instrument (Diagnostica Stago). In the standard assay, human normal pool plasma was added adjusted amount of X-CP, a factor X-activating enzyme from Russell's viper venom, to give a 30-s clotting time in the mixture of phospholid vesicles (final 10 μg/ml of 40% PE, 20% PS and 40% PC, w/v) and $CaCl_2$ (6.25 mM) in TBS containing 0.1% BSA. Clotting was initiated with $CaCl_2$ addition. APC (final 200 ng/ml) or HAPC1573 (final 20 μg/ml) was added before $CaCl_2$ addition.

Influence of mAb on APC amidolytic activity toward a chromogenic substrate. The amidolytic activity of 50 μl of 10 nM APC in HBSS buffer (HBSS containing 0.1% bovine serum albumin, 3 mM $CaCl_2$, 0.6 mM $MgCl_2$) in the absence or presence of 66.7 nM HPC1555 or HAPC1573 was determined with adding 50 μl of 0-2 mM serial diluted Spectrozyme PCa in 50 mM HEPES, 100 mM NaCl, pH 7.5 buffer.

Histone cytotoxicity assay. EA.hy926 cells were incubated with calf thymus histone H3 or H4 (Roche) in the absence or presence of 100 nM APC and 200 nM HAPC1573 in Opti-MEM medium (Invitrogen) for 1 hr at 37° C. and then 5 min at RT after 10 μg/ml propidium iodide (PI) was added. Cells were washed and detached with EDTA/PBS and subjected to flow cytometry for PI positive staining.

EXAMPLE 2

Figure 2:
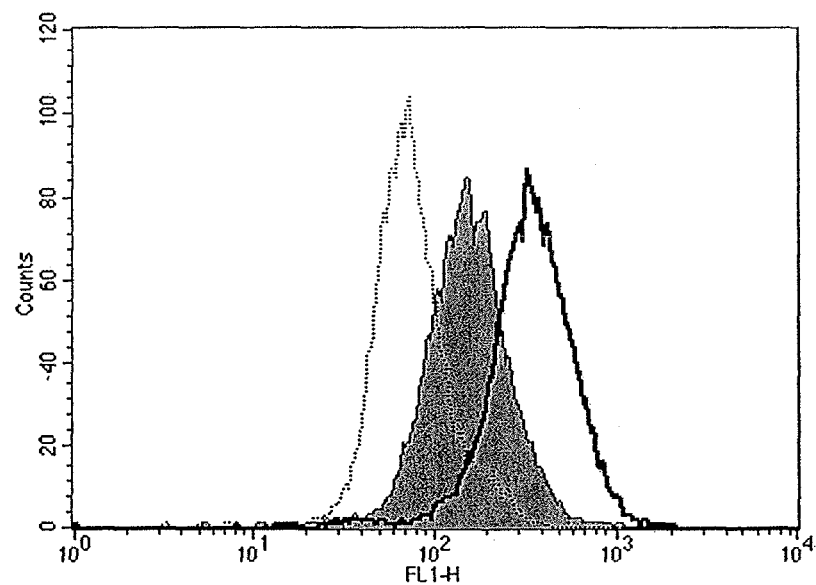
FIG. 2. HAP1573 enhances APC binding on endothelium.
Figure 3:
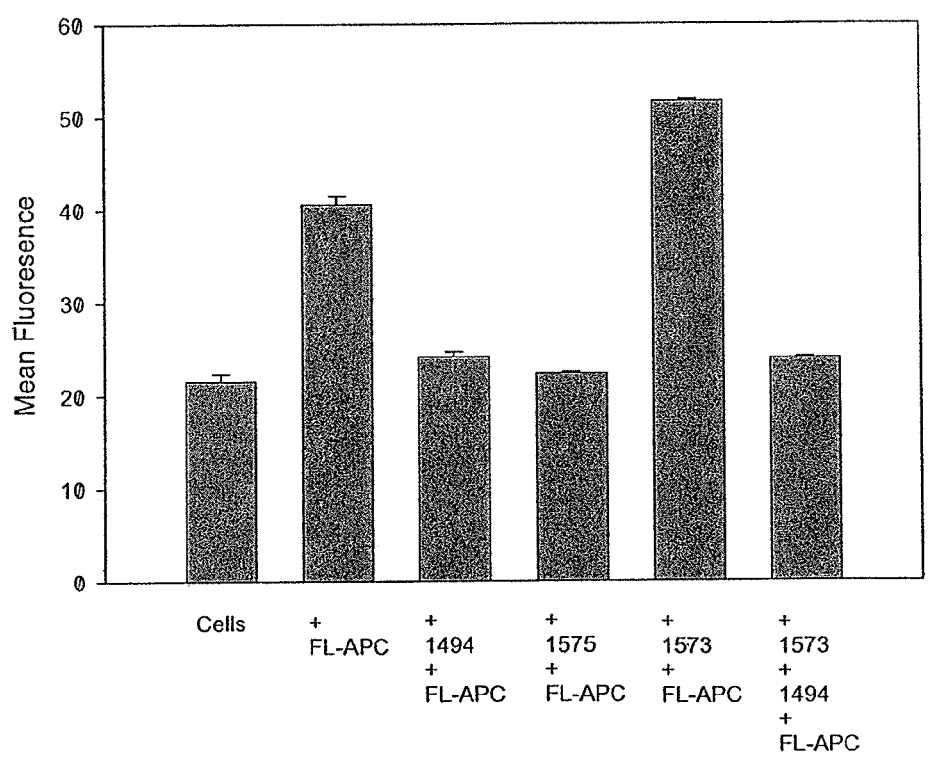
FIG. 3. HAPC1573 facilitates APC internalization into EA cells.

Results for Screening, Identification and Use of a Human MAb of the Present Invention HAPC1573 enhances APC binding on endothelium. To test whether HAPC1575 would have any influence on APC binding on endothelium, the inventors incubated EA.hy926 cells with FL-APC in the absence or presence of HAPC1573 or HPC 1575 and measured the binding of FL-APC on cells by flow cytometry. The histograph of flow cytometry showed that HAPC1573 enhanced FL-APC binding on the endothelial cells, while HPC1575 inhibited the binding of FL-APC on the cells (FIG. 2). HAPC 1573 facilitates APC internalization on endothelium FL-APC could be internalized into EA.hy926 cells through the interaction of Gla domain of APC and EPCR on the cells, and this internalization could be blocked by either EPCR blocking Ab (JRK1494) or Gla domain blocking Ab (HPC1575) (FIG. 3). HAPC1573 could facilitated FL-APC internalization into the cells, and this effect could be completely blocked by EPCR blocking Ab (FIG. 3).

Figure 4:
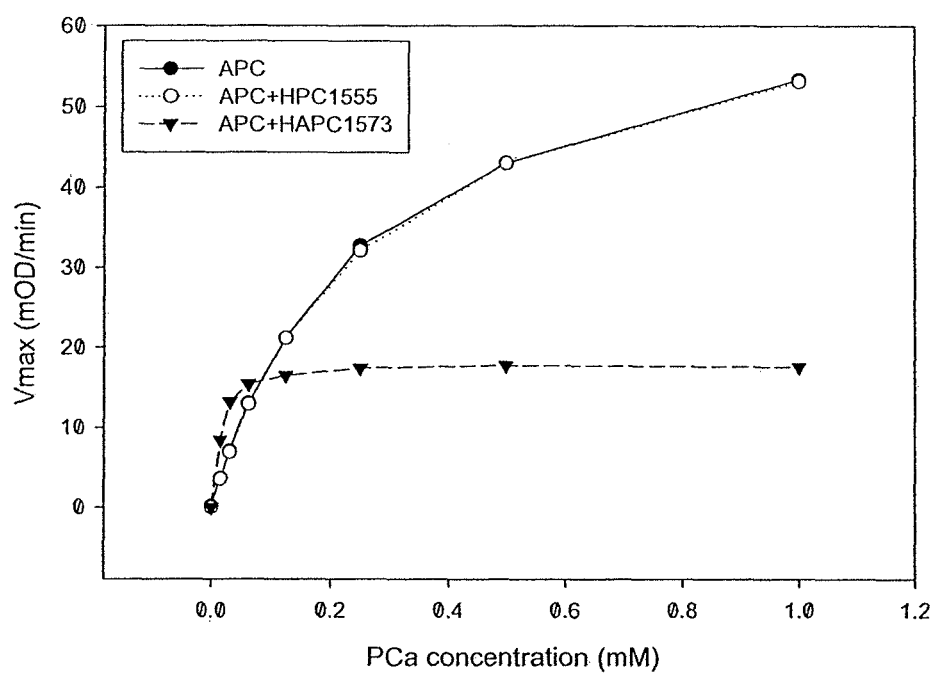
FIG. 4. HAPC1573 alters APC amidolytic activity toward a chromogenic substrate.

HAPC1573 alters APC amidolytic activity toward a chromogenic substrate. Since HAPC1573 recognized APC on the ELISA plate and on endothelial cell, the inventorsasked if HAPC1573 could affect the amidolytic activity of APC for chromogenic substrate. Synthetic peptide substrates are usually small molecules, about a few hundred Dalton molecular weight, most antibodies against serine proteases in plasma have little effect on the enzymatic activity for these small substrates. However, HAPC1573 dramatically altered the kinetic parameters of APC toward its chromogenic substrate, Spectrozyme PCa (FIG. 4). The km of APC toward Spectrozyme PCa was 15 nM in the presence of HAPC1573, compared to 270 nM in the absence of Ab or presence of HPC1555. The kcat of APC toward Spectrozyme PCa was 18 in the presence of HAPC1573, compared to 67 in the absence of Ab or in the presence of HPC1555. This profound change of APC toward small peptide substrate in the presence of HAPC1573 indicated that this mAb recognized an epitope near active site of APC and the interaction of Ab and antigen dramatically increased the affinity of APC toward small peptide substrate but decreased the off rate of product from APC catalytic site.

Figure 5:
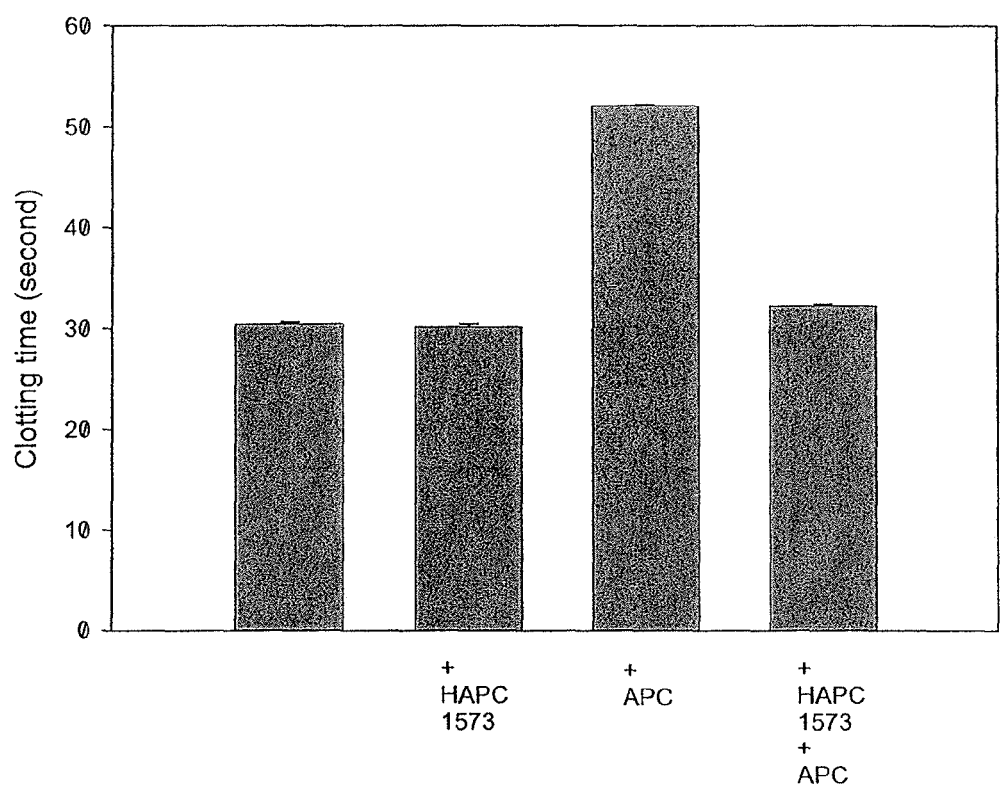
FIG. 5. HAPC1573 blocks APC anticoagulant activity in a plasma clotting assay.

HAPC1573 blocks APC anticoagulant activity in plasma. FIG. 5 showed that HAPC1573 almost completely diminished the prolongation effect of APC in factor Xa initiated one-stage plasma clotting assay, suggesting that the interaction of HAPC1573 and APC prevents APC from cleaving factor Va.

The influence of HAPC1573 on APC cleaving extracellular histones. Recently, the inventors found that APC could cleave extracellular histones and protect endothelium from cytotoxicity of histones (manuscripts in preparation). Since HAPC1573 altered APC amidolytic activity toward the chromogenic substrate and blocked APC anticoagulant activity in plasma, the inventors asked if this mAb could affect APC cleaving extracellular histone H3 and H4, and affect APC cytoprotection on endothelium against histone H3 and H4 cytotoxicity.

Figure 6:
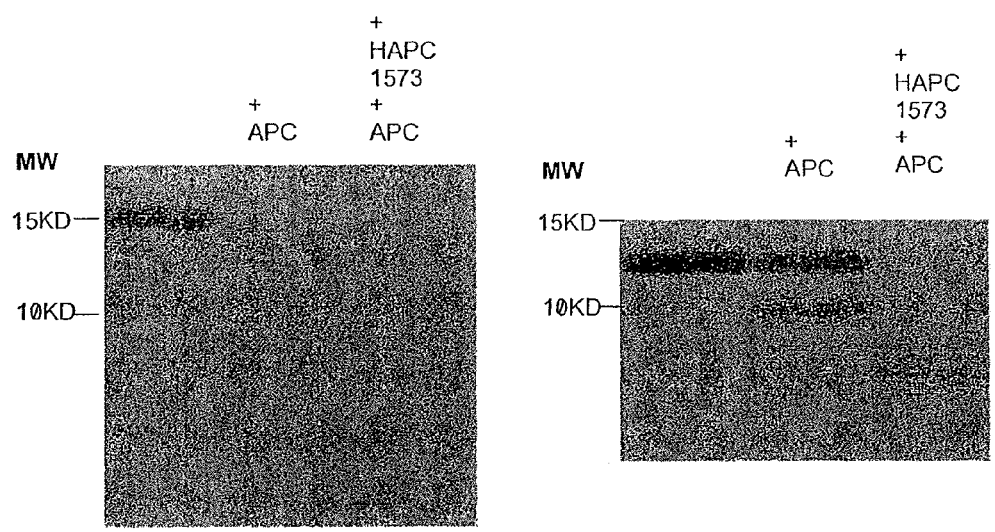
FIG. 6. HAPC1573 enhances APC cleaving histones.

Surprisingly, HAPC1573 did not inhibit but actually enhanced APC cleaving histone H3 and H4 (FIG. 6). Consistently, HAPC1573 did not inhibit but slightly enhanced APC cytoprotection activity on endothelium against histone H3 and H4 (FIG. 7).

EXAMPLE 3

Discussion for Screening, Identification and Use of a Human MAb of the Present Invention Protein C is activated by thrombin complexed with thrombomodulin on endothelium. Unlike the few-second transient life of active thrombin in vivo, human APC has about a 20 minute half-life in circulation after its generation (Berg, et al., 2003). Therefore, one may feasibly measure a level of APC in plasma to study its regulation under various pathophysical conditions.

The currently available methods to measure APC are based on an enzyme capture assay, which uses an antibody capturing APC and then measures APC activity by chromogenic substrates. Since all antibodies used in these assays recognized not only APC but also its zymogen, protein C, and since protein C concentration is about 1000 times more than APC in normal circulation, APC measurement using these methods is not clinically relevant. A rapid and robust method for APC measurement is desirable in both diagnosis and treatment. The results above show that a mAb, HAPC1573, recognizes APC but not protein C and demonstrates the development of a convenient ELISA method for measuring APC level in plasma in vivo. Typically, it takes less than 4 hours to measure a plasma sample containing 1 ng/ml APC with this method compared to 19 hours or even weeks with enzyme capture assays (Gruber and Griffen, 1992; Liaw et al., 2003).

Recent studies have shown that anticoagulant activity of APC is dispensable for its cytoprotective function, but APC cleavage activity toward PAR1 might be essential for its antiapoptotic effect (Mosnier et al., 2004). However, the cytoprotection effect of APC has been shown not only in endothelial cells which express EPCR, but also on other cells such as neuron and keratinocytes which do not express EPCR on their cell surfaces (Guo et al., 2004; Berg et al., 2003), indicating other mechanisms than PAR1 mediated APC signaling might exist. HAPC1573 altered APC cleavage activity toward a chromogenic peptide substrate and also blocked APC anticoagulant activity in a plasma clotting assay, suggesting this mAb recognizes an epitope near the APC active site and alters its catalytic activity upon antibody-antigen binding.

On the other hand, HAPC1573 did not inhibit but actually enhanced APC cleaving extracellular histones, and enhanced APC cytoprotection activity on endothelium against histones, indicating that APC anticoagulant activity for cleaving activated factor V and VIII is not required for its cytoprotection activity by cleaving extracellular histones. Cleaving extracellular histones independent from its anticoagulant activity might be one of the molecular mechanisms of APC regulation inflammation and cytoprotection.

HAPC1573 may, for example, be used in treatment of hemophilia A patients. APC cleaves both factor VIIIa and factor Va and thus negatively regulates blood clotting. In hemophilia A patients, factor VIII levels are low and the inactivation of factor Va by APC is probably a major pathway to regulate hemostasis and thrombosis in these patients. Recent clinical reports demonstrated factor V Laiden mutant which is resistant to APC cleavage was beneficial to hemophilia A patients regarding their bleeding symptom (van't Zant et al., 1997). Blocking APC anticoagulant activity toward factor Va in vivo by a mAb such as HAPC1573 might be an alternative approach for hemophilia A treatments, especially for those patients who have high level factor VIII inhibitors so that the factor VIII replacement therapy would not be very effective.

Another possible clinical application of HAPC1573 is in the treatment of trauma patients wherein homeostasis is disrupted, excessive bleeding is likely, and surgical intervention is delayed to regain homeostatis. Treatment with HAPC1573 can selectively restore the pro-coagulant state without eliminating the cytoprotective or anti-inflammatory activities of activated protein C.

Another possible clinical application of HAPC1573 is its combination with APC in sepsis treatment. APC is currently the only FDA approved medication for severe sepsis. Its bleeding side effect in patients is due to APC anticoagulant activity. HAPC1573 blocked APC anticoagulant activity while maintained and even enhanced APC cytoprotective effect. This mAb-APC complex might be a better therapeutic than APC alone regarding its bleeding side effect.

EXAMPLE 4

Methods for Screening and Use of a Mouse Monoclonal Antibody of the Present Invention Materials and Methods. Recombinant mouse protein C, APC, rat mAb MPC1609 and MAPC1591 were produced in this lab according to the standard procedures. Fluorescein labeled APC (FL-APC) was prepared with the Fluorescein-EX Protein Labeling Kit from Molecular Probes according to the manufacturer's instructions.

Animal study. Six to 12 week male BL6 mice were used in this study according to the animal protocol approved by Institutional Animal Care and Use Committees of the Oklahoma Medical Research Foundation.

Cell culture. bEnd3 cells (mouse brain derived endothelial cell line) were cultured in DMEM (Dulbecco's modified Eagle's medium) supplemented with 10% fetal bovine serum and L-glutamine. EA.hy926 cells (human endothelial cell line) were cultured in DMEM supplemented with 10% fetal bovine serum, L-glutamine and HAT (hypoxanthine, aminopterin, thymidine).

FL-APC binding and protein C activation on endothelium. bEnd3 cells were incubated with 100 nM FL-APC in HBSS buffer containing 0.5% BSA, 3 mM $CaCl_2$ and 0.6 mM $MgCl_2$ in the absence or presence of 125 nM MPC1609 or MAPC1591 for 15 minute on ice, and subjected to FACS analysis.

The influence of mAb on protein C activation on endothelial cells. bEnd3 cells in 24-well plate were washed once with HBSS buffer (HBSS containing 0.1% bovine serum albumin, 3 mM $CaCl_2$, 0.6 mM MgCl2) and preincubated for 5 min with HBSS buffer containing 0.1 µM protein C with 0.1 µM MPC1609 or MAPC1591. The activation reactions were initiated by addition of 5 nM bovine thrombin in a total volume of 0.2 ml. After 15 min at 37° C., the reactions were stopped by adding 50 µl of bovine anti-thrombin III (1.67 mg/ml) to the reactions. Fifty µl supernatants were transferred to the 96-well microplate, and the activation rate of protein C were determined with Vmax at 405 nm toward 50 µl of 0.4 mM Spectrozyme PCa substrate in 100 mM NaCl, 50 mM HEPES-NaOH, pH 7.5 buffer.

APC anti-coagulant activity assay. The influence of mAb on APC anti-coagulant activity in plasma was determined in a modified factor Xa one-stage clotting assay using ST4 coagulation instrument (Diagnostica Stago). In this assay, plasma (50% mouse plasma and 50% human normal pool plasma) was added adjusted amount of X-CP, a factor X-activating enzyme from Russell's viper venom, to give a 30-s clotting time in the mixture of phospholipid vesicles (final 10 µg/ml of 40% phosphatidylethonalamine, 20% phosphatidylserine and 40% phosphatidylcholine, w/v) and $CaCl_2$ (6.35 nM) in 20 mM Tris-HCl, 150 mM NaCl buffer (pH 7.5) containing 0.1% BSA. Clotting was initiated with $CaCl_2$ addition. APC (final 200 ng/ml) and MPC1609 (final 5 µg/m1) or MAPC1591 (final 5 µg/ml) were added before $CaCl_2$ addition.

Histone cytotoxicity assay. EA.hy926 cells were incubated with 50 µg/ml calf thymus histones (Sigma) in the absence or presence of 100 nM APC and 200 nM MAPC1591 in Opti-MEM medium (Invitrogen) for 1 hr at 37° C. and then 5 min at RT after 10 µg/ml propidium iodide (PI) was added. Cells were washed and detached with 0.526 mM EDTA in PBS and subjected to flow cytometry for PI-positive staining.

IL-6, BUN and creatinine assay. Mouse serum was analyzed on Vitros 250 Chemistry Analyzer (Ortho-Clinical Diagnostics) for BUN and creatinine. Serum IL-6 was measured by Quantikine Colorimetric Sandwich ELISA (R&D Systems).

EXAMPLE 5

Figure 8C:
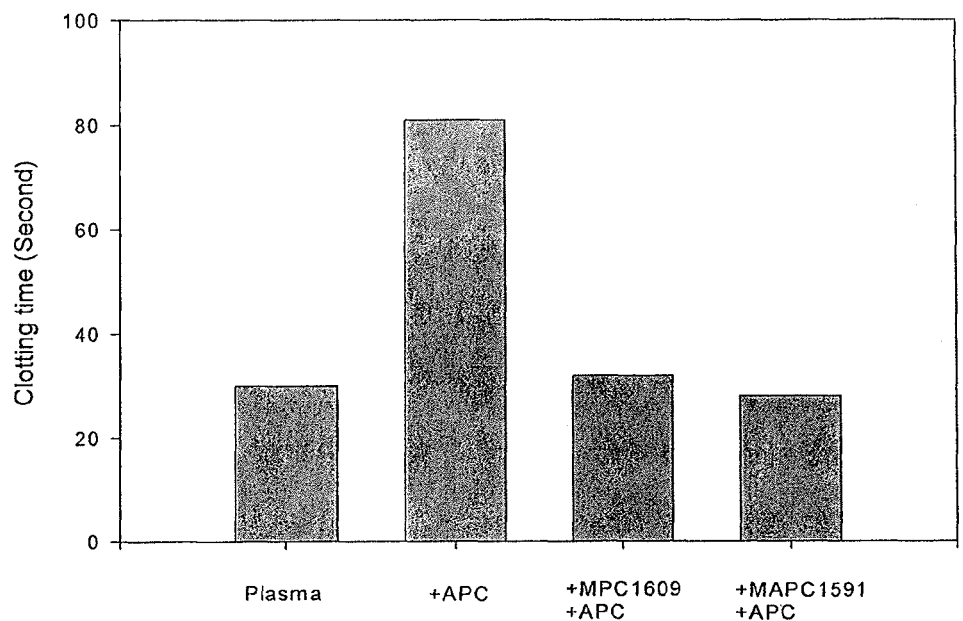

Results for Screening and Use of a Mouse Monoclonal Antibody of the Present Invention MPC1609 was against both protein C and APC, and could inhibit protein C and APC binding on endothelium (FIG. 8A and data not shown). MAPC1591 was against APC but not protein C and could enhance APC binding on endothelium (FIG. 8A and data not shown). Protein C activation on endothelium was dramatically decreased in the presence of MPC1609 (FIG. 8B). MAPC1591 also decreased protein C activation to some extent probably due to its enhancement of APC binding on the cells (FIG. 8B). Both MPC1609 and MAPC1591 could completely inhibit APC anti-coagulant activity in plasma clotting assay (FIG. 8C). Based on these in vitro studies, the inventors concluded that MPC1609 inhibited protein C and APC binding on endothelium or phospholipid by masking the Gla-domain of protein C or APC which was responsible for the binding of protein C or APC on endothelium or phospholipid. MAPC1591 recognized APC but not protein C through interacting with an epitope around the active site of APC and this interaction inhibited APC anti-coagulant activity likely by preventing APC cleaving factor Va.

Figure 9:
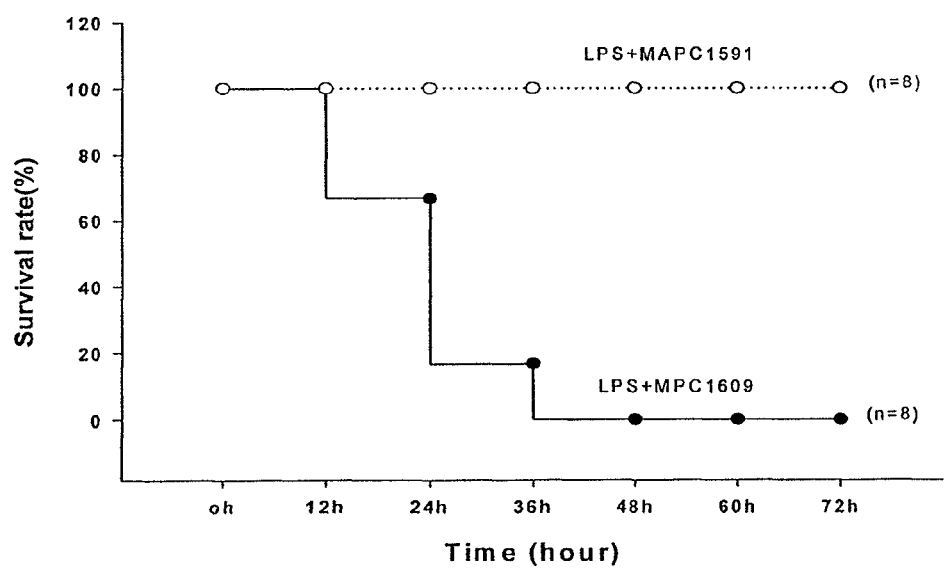
FIG. 9. MPC1609 but not MAPC1591 exacerbated mice into lethality with sublethal dose of LPS. BL6 mice were injected intravenously with 10 mg/kg LPS with 10 mg/kg MPC1609 or MAPC1591 and survival rates were indicated.
Figure 10A:
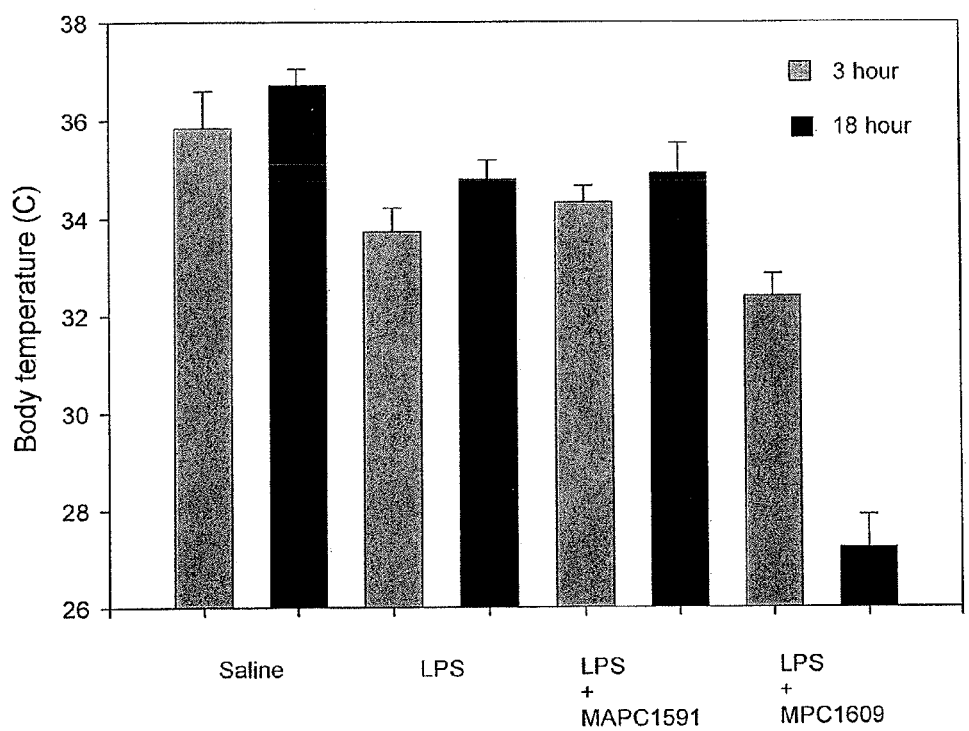
FIGS. 10A-D. Body temperature, serum IL-6, BUN and creatinine levels of mice challenged with LPS and MPC1609 or MAPC1591. BL6 mice (4 mice for each group) were injected intravenously with saline, 10 mg/kg LPS, or 10 mg/kg LPS with 10 mg/kg MPC1609 or MAPC1591.
Figure 10B:
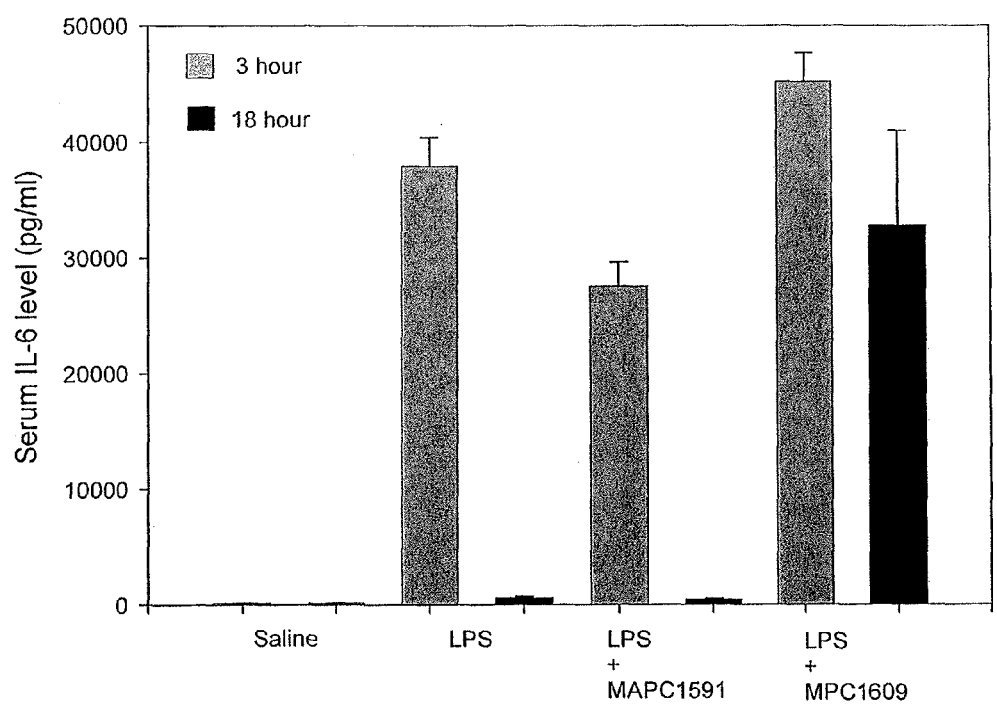
Figure 10C:
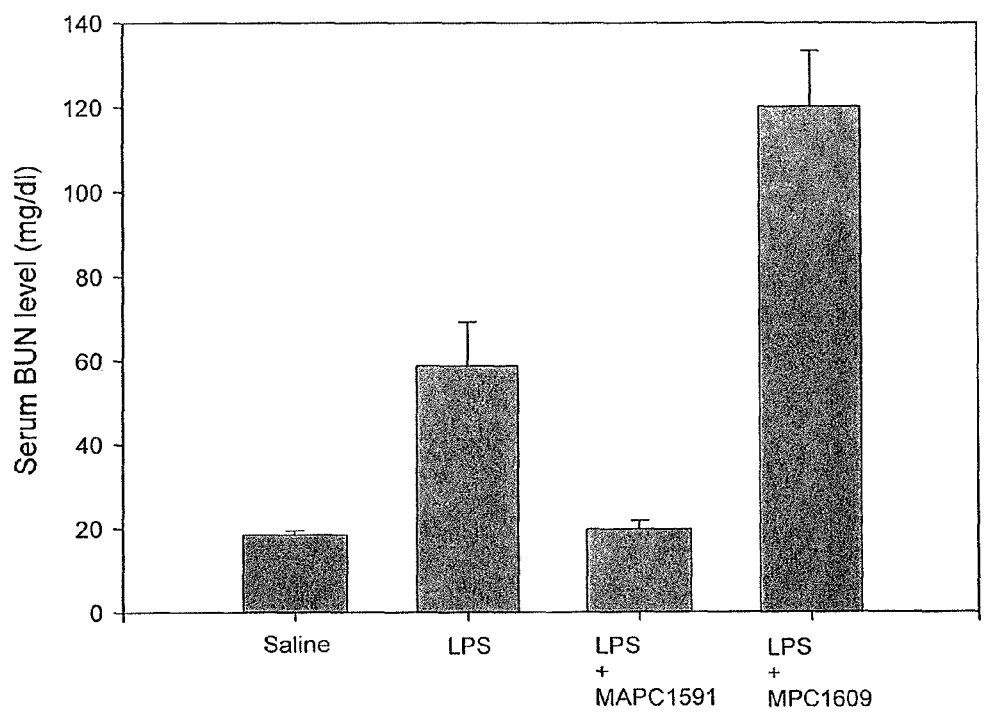
Figure 10D:
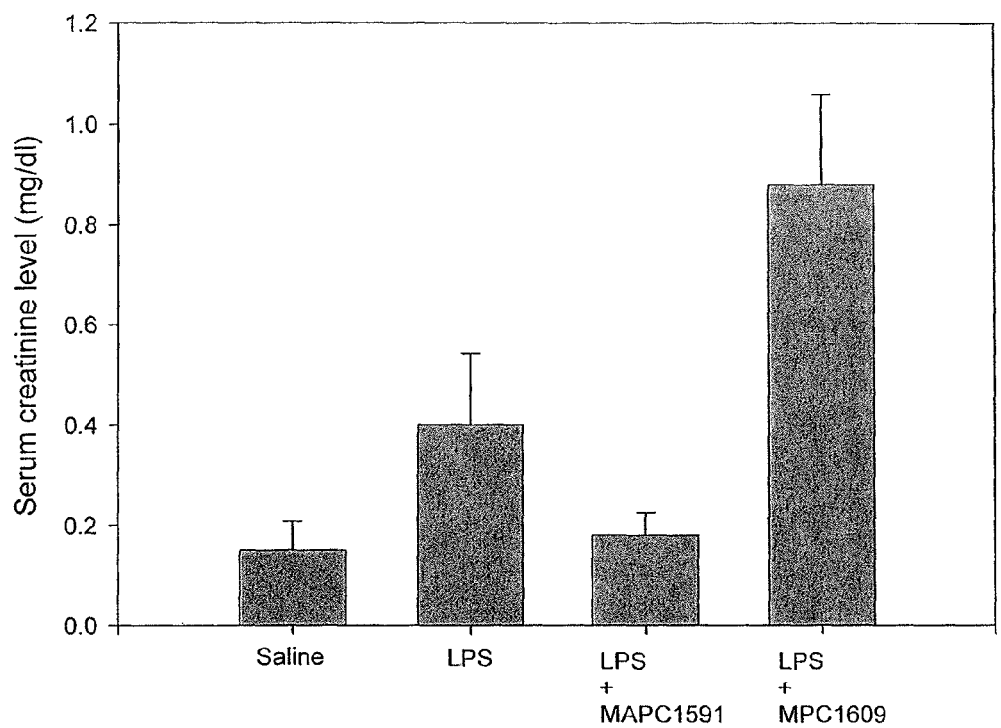

To explore the molecular mechanism of APC protective effect in LPS induced septic shock, the inventors injected sublethal dose of LPS with MPC1609 or MAPC1591 into mice and they found that mice injected LPS and MPC1609 all died within 48 hrs, mice injected LPS and MAPC1591 all survived (FIG. 9). 18 hour after infusion, mice injected with LPS and MPC1609 showed severe septic shock symptoms including low body temperature, high neutrophil, low lymphocyte and low platelet counts in peripheral blood (FIG. 10A and data not shown). Serum IL-6 level was extremely higher in these mice (FIG. 10B), but no significant difference of IL-6 mRNA level in heart, lung, liver, spleen, thymus and peripheral blood was observed between these mice and mice injected with LPS plus MAPC1591 (data not shown), suggesting that de novo synthesis of IL-6 might not be a major cause for the sustained higher IL-6 level in the septic shocked mice. Serum BUN and creatinine levels in mice injected with LPS and MPC1609 were higher than other mice (FIG. 10C and FIG. 10D) indicated acute renal failure occurred in these mice which might contribute a slow clearance of IL-6. Interestingly, BUN and creatinine levels in mice injected with LPS and MAPC1591 were even lower than the levels in mice injected with LPS alone (FIG. 10C and FIG. 10D), suggesting that MAPC1591 and APC complex might be more effective than APC for the renal protection in vivo under LPS challenge.

Figure 11C:
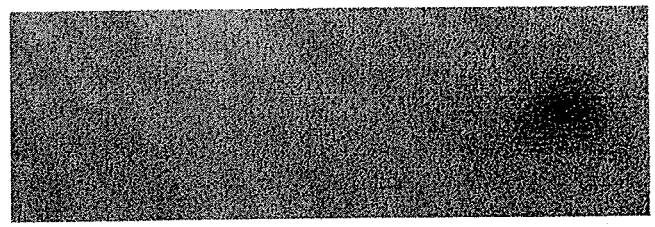

Extracellular histones were found on activated neutrophil and macrophages, and apoptotic cells (Brinkmann et al., 2004; Radic et al., 2004), and they were cytotoxic toward mammalial cells (Abakushin et al., 1999; Currie et al., 1997; Kleine et al., 1997). APC could cleave histone H3 and histone H4, and MAPC1591 did not inhibit but actually enhanced APC cleaving these histones (FIG. 10A). APC could reduce the cytotoxicity of histones toward endothelium and MAPC1591 could enhance this APC cytoprotective activity (FIG. 11B). Extracellular histone was indeed detected in the septic mouse serum after LPS and MPC1609 injection but not in the mice injected with LPS or LPS and MAPC1591 (FIG. 11C), indicating an in vivo correlation between the deficient protein C activation, presence of extracellular histone in the circulation and lethality of mice under septic shock. Taking these in vitro data together with in vivo observations, the inventors could distinguish the cytoprotective activity of APC from its anticoagulant activity by MAPC 1591, and cleaving cytotoxic histones by APC independent of its anticoagulant activity provides a new molecular mechanism of APC preventing mice from LPS induced septic shock.

EXAMPLE 6

Discussion for Screening and Use of a Mouse Monoclonal Antibody of the Present Invention The protein C pathway plays an important role in regulating both blood coagulation and inflammation (Esmon, 2006). Human APC was demonstrated to significantly reduce mortality in severe sepsis and has been approved as the first medication for severe sepsis treatment (Bernard et al., 2001). However, the molecular mechanism of APC protective effects in sepsis is still poorly understood. Mutagenesis study indicated that anticoagulant activity of APC was apparently dispensable for APC anti-apoptotic effect on endothelial cells (Mosnier et al., 2004), and anti-inflammation and anti-apoptotic effects of APC signaling were protease activated receptor 1 (PAR-1) mediated in endothelial cells (Reiwald et al., 2002). However, PAR-1-deficient mice had similar phenotype to its wild-type control mice under LPS challenge, suggesting that PAR-1 might not be a major player for APC to regulate inflammation and cytoprotection in vivo (Pawlinski et al., 2004; Camerer 2006). Given a central role of APC in regulating pathophysical functions in vivo, the inventors generated two mAbs against mouse protein C and mouse APC and used these two mAbs to explore the poorly understood mechanisms of APC protective effect in LPS induced septic shock in mice.

\*\*\*

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

G. References

References mentioned throughout this application, including the following references, to the extent that they provide exemplary procedural or other details supplementary to those set forth herein, are specifically incorporated herein by reference:

U.S. Pat. No. 4,196,265
Abakushin et al., *Biochemistry (Most.)*, 64:693-698, 1999.
Antibodies: A Laboratory Manual, Cold Spring Harbor Laboratory, Cold Spring Harbor Press, Cold Spring Harbor, N.Y., 1988.
Beidler et al., *J. Immunol.*, 141:4053-4060, 1988.
Berg et al., *Proc. Natl. Acad. Sci. USA*, 100:4423-4428, 2003.
Bernard et al., *New England J. Medicine*, 344:699-709, 2001.
Better et al., *Science*, 240:1041-1043, 1988.
Brinkmann, *Science*, 203:1532-1535, 2004.
Camerer, *Blood*, 107:3912-3921, 2006.
Currie et al., *Biochim. Biophys. Acta*, 1355:248-258, 1997.
EP Appin. 125,023
EP Appin. 171,496
EP Appin. 173,494
EP Appin. 184,187
Esmon, In: *Natural anticoagulants and their pathways*, Handbook of Exper. Pharm., 132:447-476, Born et al. (Eds.), Springer-Verlag, NY, 1999.
Esmon, *J. Biol. Chem.*, 264; 4743- 4746, 1989.
Esmon, *Proteolytic Enzymes in Coagulation, Fibrinolysis, and Complement Activation*, Part A, 222:359-385, 1993.
Esmon, *Semin. Thromb. Hemost.*, 32 Suppl 1:49-60, 2006.
Gruber and Griffin, *Blood*, 79:2340-2348, 1992.
Guo et al., *Neuron.*, 41:563-572, 2004.
Jones et al., *Nature*, 321:552-525, 1986.
Kleine et al., *Am. Physiol* 273:C1925-C1936, 1997.
Liaw et al., *J. Thrombosis and Haemostasis*, 1:662-670, 2003.
Liu et al., *J. Immunol.*, 139:3521-3526, 1987.
Liu et al., *Proc. Natl. Acad. Sci. USA*, 84:3439-3443, 1987.
Morrison, *Science*, 229:1202-1207, 1985.
Mosnier et al., *Blood*, 104:1740-1744, 2004.
Nishimura et al., *Canc. Res.*, 47:999-1005, 1987.
Oi et al., *BioTechniques*, 4:214, 1986.
Pawlinski et al., *Blood*, 103:1342-1347, 2004.
PCT Appin. PCT/U.S.86/02269
PCT Appin. WO 86/01533
Radic et al., *J. Immunol.*, 172:6692-6700, 2004.
Remington's Pharmaceutical Sciences, 18th Ed., Mack Printing Company, 1289-1329, 1990.
Remington's Pharmaceutical Sciences, 15th Ed., 1035-1038 and 1570-1580, 1990.
Rezaie and Esmon, *J. Biol. Chem.*, 267:26104-26109, 1992.
Riewald et al., *Science*, 296:1880-1882, 2002.
Shaw et al., *J. Natl. Cancer Inst.*, 80:1553-1559, 1988.
Sun et al., *Proc. Natl. Acad. Sci. USA*, 84:214-218, 1987.
van't Zant et al., *Blood*, 90(8):3067-3072, 1997.
Verhoeyan et al., *Science*, 239:1534, 1988.
Wood et al., *Nature*, 314:446-449, 1985.

What is claimed is:

1. A method of treating a subject suffering from hemophilia comprising administering an effective amount of a monoclonal antibody, wherein said antibody binds to activated protein C and inhibits anticoagulant activity but does not bind to or inhibit activation of unactivated protein C, to said subject.

* * * * *